(12) United States Patent
Matsuo et al.

(10) Patent No.: US 7,842,509 B2
(45) Date of Patent: Nov. 30, 2010

(54) BLOOD ANALYZER AND BLOOD ANALYZING METHOD

(75) Inventors: Naohiko Matsuo, Kobe (JP); Susumu Hoshiko, Kobe (JP); Norimasa Yamamoto, Kobe (JP); Mitsuyo Ito, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/730,229

(22) Filed: Mar. 30, 2007

(65) Prior Publication Data

US 2007/0248490 A1    Oct. 25, 2007

(30) Foreign Application Priority Data

Mar. 30, 2006    (JP) .............................. 2006-092813

(51) Int. Cl.
*G01N 15/06* (2006.01)
(52) U.S. Cl. .................. 436/164; 422/63; 422/68.1; 422/81; 422/82.05; 422/82.09
(58) Field of Classification Search ................ 436/164; 422/63, 68.1, 82.09, 81, 82.05
See application file for complete search history.

(56) References Cited

U.S. PATENT DOCUMENTS

| | | | |
|---|---|---|---|
| 4,731,225 A * | 3/1988 | Wakatake | 422/65 |
| 5,002,392 A | 3/1991 | Swope et al. | |
| 5,100,622 A * | 3/1992 | Mimura et al. | 422/67 |
| 5,646,046 A * | 7/1997 | Fischer et al. | 436/49 |
| 5,734,468 A | 3/1998 | McNeal | |
| 6,269,313 B1 | 7/2001 | Givens et al. | |

FOREIGN PATENT DOCUMENTS

| | | | |
|---|---|---|---|
| JP | 57-59151 A | | 4/1982 |
| JP | 6-66808 A | | 3/1994 |

\* cited by examiner

*Primary Examiner*—Lyle A Alexander
*Assistant Examiner*—Dennis M White
(74) *Attorney, Agent, or Firm*—Sughrue Mion, PLLC

(57) ABSTRACT

A blood analyzer has a light emitter for emitting light to an analysis sample which is a mixture of a blood specimen and a reagent. It also has a light receiver for receiving light of a plurality of wavelengths from the analysis sample over time, and for acquiring data of the amount of the received light corresponding to each of the wavelengths at a plurality of points of time. A selector selects the data corresponding to one of the wavelengths, based on the change of the amount of received light over time in the data acquired by the light receiver. An analysis section analyzes a characteristic of the blood specimen using the data which are selected by the selector. A blood analyzing method is also described.

24 Claims, 11 Drawing Sheets

BLOOD ANALYZER AND BLOOD ANALYZING METHOD

CROSS-REFERENCE TO RELATED APPLICATIONS

This application claims priority from Japanese Patent Application 2006-092813 filed on Mar. 30, 2006, the disclosure of which is herein incorporated by reference in its entirety.

FIELD OF THE INVENTION

The present invention relates to a blood analyzer and blood analyzing method, and specifically relates to a blood analyzer and blood analyzing method for optically analyzing analysis samples prepared by adding reagent to a blood specimen.

BACKGROUND

Blood coagulation analyzers are known which prepare an analysis sample by adding a blood-coagulating reagent to a blood sample, and analyze the coagulation time of the blood by optically measuring the process of a coagulation reaction in the analysis sample. For the sake of generality, such an analysis sample made by adding a reagent to blood or made in any other manner may be referred to as a blood coagulation analysis sample.

In blood coagulation analysis, interference substances such as hemoglobin, bilirubin chyle and the like present in the analysis sample (substances that optically interfere with the measurement of a target material and coexist in the sample together with the target material (for example, fibrinogen) being examined) may influence the optical measurement and hinder accurate analysis.

When measurement is performed using long wavelength light (for example, 800 nm), hemoglobin and bilirubin do not affect the measurement and chyle only slightly affects the measurement, however, measurement sensitivity is low.

Furthermore, the coagulation reaction changes the amount of light transmitted through the sample material, the change is proportional to the amount of coagulation factor (for example, fibrinogen) contained in the analysis sample. Therefore, there is little change in the amount of light in an analysis sample that has a low coagulation factor content, and accurate analysis can not be performed under long-wavelength light that has low measurement sensitivity.

Therefore, in conventional blood coagulation analyzers use light at a wavelength in the vicinity of 660 nm for measurement to obtain suitable sensitivity wherein the interference substances do not influence very much so that the analyzers can perform analysis adequately.

Conventionally, the interference substances present in a sample (serum and the like) are measured prior to performing the main measurement (for example, biochemical analysis) (for example, refer to Japanese Laid-Open Patent Publication Nos. S57-59151 and H06-66808, and U.S. Pat. No. 5,734,468).

In the measuring method for degree of chyle, jaundice and hemolysis in serum disclosed in Japanese Laid-Open Patent Publication No. S57-59151, serum is irradiated by light at four wavelengths, and light absorption is primarily measured using short-wavelength light within the visible range (for example, 410 nm), and a serum sample that has measured light absorption greater than a fixed value is determined to be abnormal due to chyle and jaundice and hemolysis. Then, secondly the serum sample that has been determined to be abnormal is subjected to determination of the degree of chyle, jaundice, and hemolysis by comparing the light absorption measured at four wavelengths with several preset standards.

In the chromogen (interference substance) measurement method disclosed in Japanese Laid-Open Patent Publication No. 6-66808, a sample blank liquid is prepared by mixing a blank reaction reagent with a specimen including suspension material (hemoglobin, bilirubin, chyle and the like), and measuring the degree of interference substance by irradiating the sample blank liquid with light at four wavelengths that include a wavelength at which the light is absorbed by chyle, and substantially not absorbed by hemoglobin and bilirubin. Specifically, the degree of chyle is calculated by assuming the degree of absorption represented by an exponential function of the wavelength, and determining a wavelength-absorption regression curve. Moreover, the amounts of hemoglobin and bilirubin are calculated by assuming a preset fixed relationship between absorptions at different wavelengths, and preparing and solving simultaneous linear equations related to the optical absorbance at the measurement wavelength.

In the analyzer for determining the presence of hemolysis, jaundice, and lipemia in a serum sample disclosed in U.S. Pat. No. 5,734,468, the optical absorption of a serum sample in a needle tube is first measured by irradiating the serum sample aspirated into the needle tube disposed in a transparent part provided with a probe using light emitted from light emitting diodes. Then, a serum sample that has been determined to be measurable based on this optical absorption is transferred to a clinical analyzer where a main measurement is performed.

In the conventional blood coagulation analyzers described above, the measurement wavelength is set with regard to the possibility that a sample contains interference substances. However, there are various contents of interference substances and coagulation factors depending on the sample, and the optimum wavelength for measurement will vary sample by sample. Therefore, conventional blood coagulation analyzers can only measure at preset wavelengths, thus reducing analysis accuracy.

SUMMARY

The scope of the present invention is defined solely by the appended claims, and is not affected to any degree by the statements within this summary. A first blood analyzer embodying features of the present invention includes: a light emitter for emitting light to an analysis sample which is a mixture of a blood specimen and a reagent; a light receiver for receiving light of a plurality of wavelengths from the analysis sample over time, and for ouputting data of the amount of the received light corresponding to each of the wavelengths at a plurality of points of time; a selector for making a selection of the data corresponding to one of the plurality of wavelengths, the selection being based on a change, of an amount of light received over time, represented in the data output by the light receiver; and an analysis section for analyzing a characteristic related to blood coagulation of the blood specimen using the data which are selected by the selector.

A second blood analyzer embodying features of the present invention includes: a light emitter for emitting light to an analysis sample which is a mixture of a blood specimen and a reagent; a light receiver for receiving light of a plurality of wavelengths from the analysis sample over time, and for ouputting data of the amount of the received light corresponding to each of the wavelengths at a plurality of points of time; a selector for making a selection of the data corresponding to one of the plurality of wavelengths, the selection being based on a change, of an amount of light received over time, represented in the data output by the light receiver; and an analysis section for analyzing a characteristic of the blood specimen using the data which are selected by the selector.

A first blood analyzing method embodying features of the present invention includes steps of: a) emitting light to an analysis sample prepared using a blood specimen; b) storing data, representing an amount of light received from the blood coagulation analysis sample, for each of a plurality of light wavelengths, at a plurality of points in time; c) selecting the stored data corresponding to one of the plurality of wavelengths, based on a change, of the amount of light received light received over time, represented in the stored data; and d) analyzing a characteristic related to blood coagulation of the blood specimen using the data which are selected in step c).

A second blood analyzing method embodying features of the present invention includes steps of: a) emitting light to an analysis sample prepared using a blood specimen; b) storing data, representing an amount of light received from the blood coagulation analysis sample, for each of a plurality of light wavelengths, at a plurality of points in time; c) selecting the stored data corresponding to one of the plurality of wavelengths, based on a change, of the amount of light received light received over time, represented in the stored data; and d) analyzing a characteristic of the blood specimen using the data which are selected in step c).

DETAILED DESCRIPTION OF THE PREFERRED EMBODIMENTS

The embodiments of the present invention are described hereinafter based on the drawings.

Figure 1:
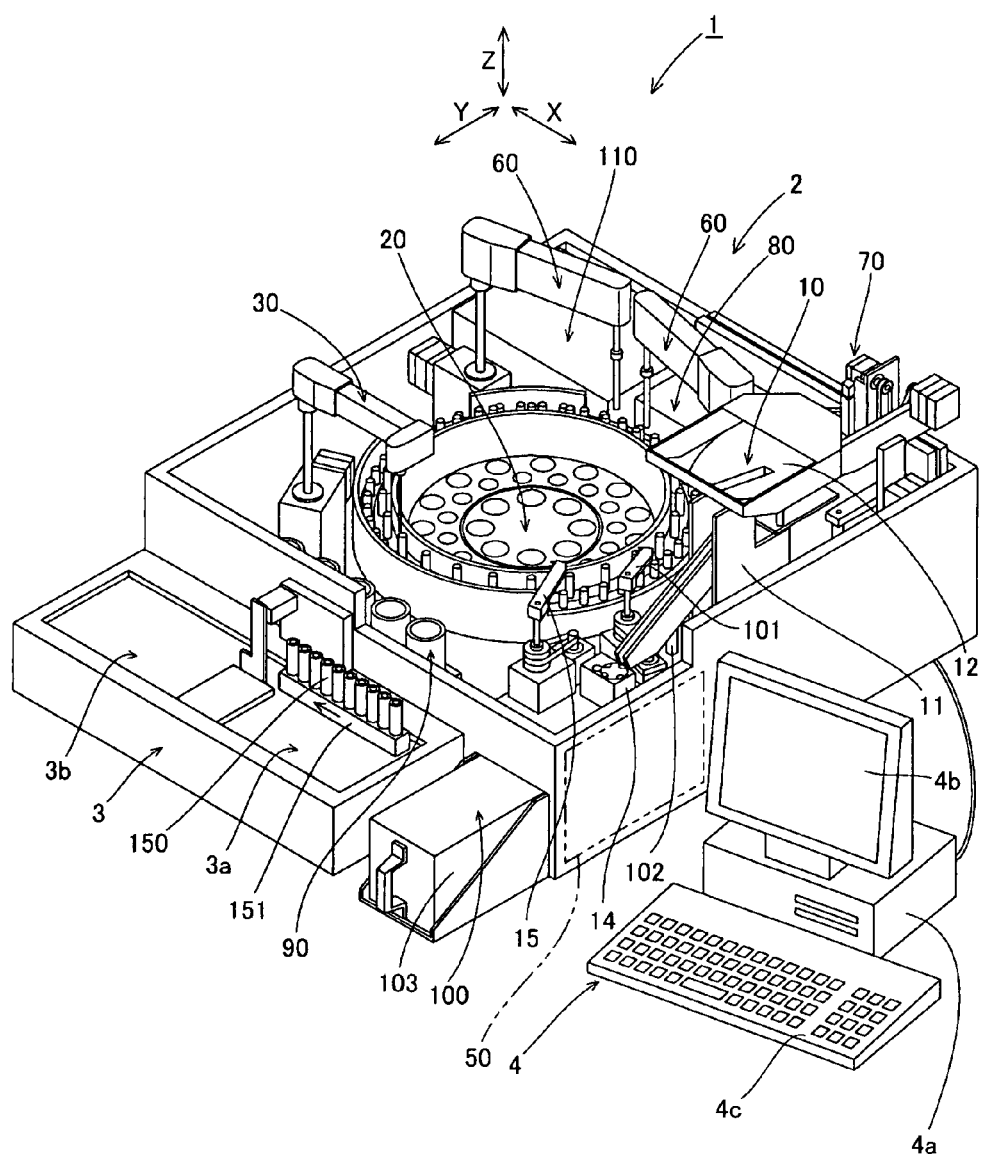
FIG. 1 is a perspective view showing the general structure of an embodiment of the blood coagulation analyzer of the present invention.
Figure 2:
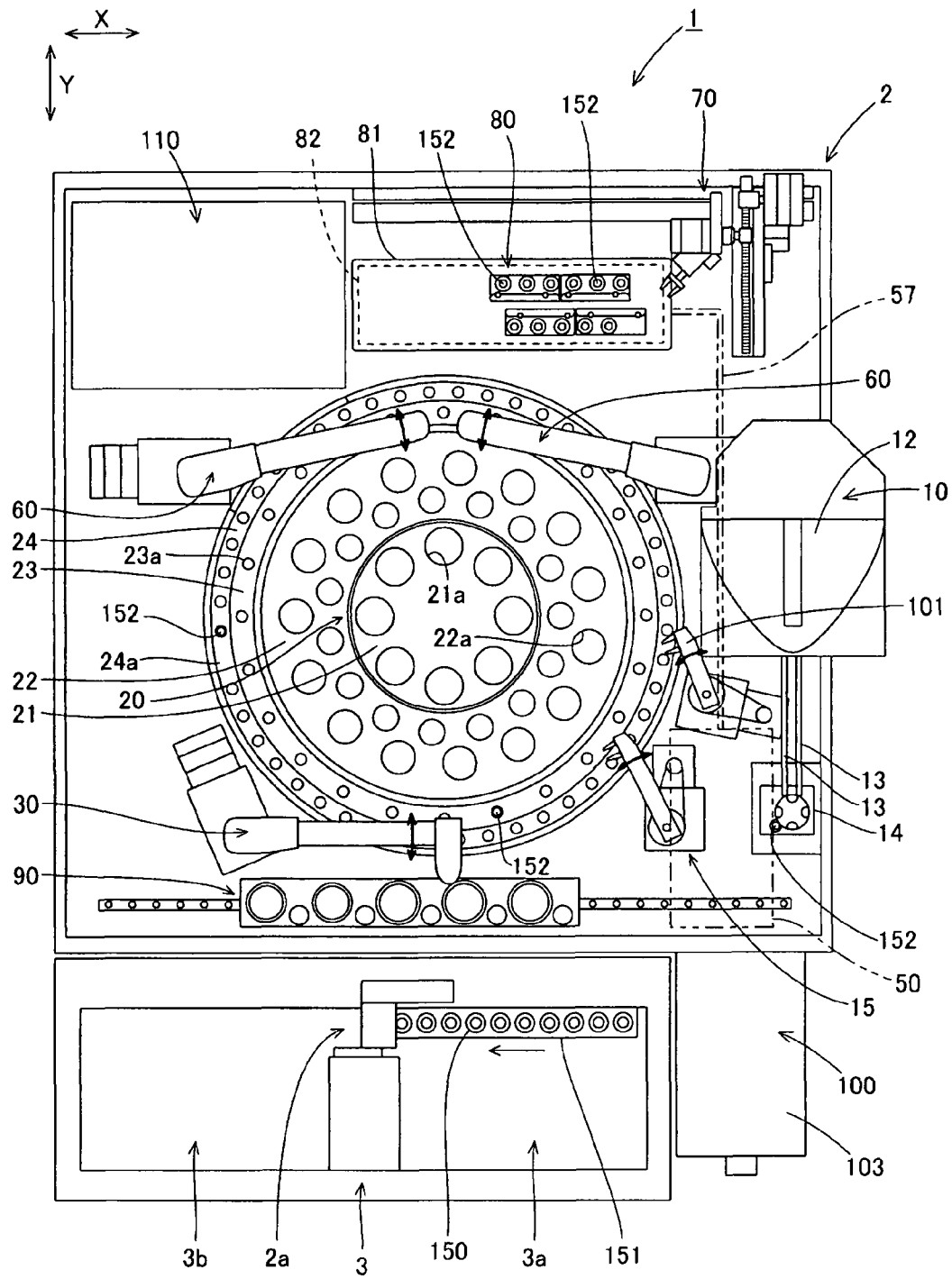
FIG. 2 is a top view showing the detection mechanism and transport mechanism of the blood coagulation analyzer of the embodiment of FIG. 1.

FIG. 1 is a perspective view showing the general structure of an embodiment of the blood coagulation analyzer of the present invention. FIG. 2 is a top view showing the detection mechanism and transport mechanism of the blood coagulation analyzer of the embodiment of FIG. 1. FIGS. 3 through 14 illustrate the structure of the blood coagulation analyzer of the embodiment of FIG. 1. The general structure of an embodiment of the blood coagulation analyzer 1 of the present invention is described below with reference to FIGS. 1 through 14.

This embodiment of the blood coagulation analyzer 1 of the present invention optically measures and analyzes the degree of activity and amount of specific substances related to blood coagulation and fibrinolysis, and uses blood plasma as a specimen (blood sample). In the blood coagulation analyzer 1 of the present embodiment, the specimen coagulation time is analyzed by optically measuring the specimen using a coagulation time method. Measurement items include PT (prothrombin time), APTT (active partial thromboplastin time), and Fbg (fibrinogen content) and the like.

As shown in FIG. 1, the blood coagulation analyzer 1 comprises a detection device 2, transport device 3 disposed in front of the detection device 2, and a control device 4 electrically connected to the detection device 2.

The transport device 3 has the function of transporting a rack 151 holding a plurality of test tubes 150 (ten tubes in the present embodiment) that contain specimens to an aspiration position 2a (refer to FIG. 2) of the detection device 2 so as to supply specimen to the detection device. Furthermore, the transport device 3 has a rack set region 3a that accommodates the racks 151 that hold the test tubes 150 containing unprocessed specimens, and a rack receiving region 3b that accommodates the racks 151 that hold test tubes 150 containing processed specimens.

The detection device 2 is configured to obtain optical information relating to a supplied specimen by optically measuring a specimen supplied from the transport device 3. In the present embodiment, optical measurement is performed on a specimen dispensed into a cuvette 152 (refer to FIG. 2) of the detection device 2 from a test tube 150 loaded in the rack 151 of the transport device 3. Furthermore, the detection device 2 includes a cuvette supplier 10, rotating part 20, specimen dispensing arm 30, lamp unit 50, two reagent dispensing arms 60, cuvette transporter 70, photometric part 80, rush specimen acceptor 90, cuvette disposal 100, and fluid provider 110, as shown in FIGS. 1 and 2.

The cuvette supplier 10 is configured to sequentially supply a plurality of cuvettes 152 directly inserted by a user to the rotating part 20. As shown in FIGS. 1 and 2, the cuvette supplier 10 includes a hopper 12 mounted on the device body via a bracket 11, two induction plates 13 provided below the hopper 12, support base 14 disposed at the bottom end of the two induction plates 13, and catcher 15 provided at a predetermined distance from the support base 14. The two induction plates 13 are disposed so as to be mutually parallel with a space therebetween so as to be smaller than the diameter of the flange of the cuvette 152 and larger than the diameter of the barrel of the cuvette 152. The cuvettes 152 supplied into the hopper 12 are configured so as to move smoothly toward the support base 14 with the flange engaged at the top surface of the two induction plates 13. Furthermore, the support base 14 functions to rotate the cuvette 152 that has fallen between the induction plates 13 to a position at which the cuvette 152 can be grabbed by the catcher 15. The catcher 15 is provided to supply the cuvette 152, which has been moved by the support base 14, to the rotating part 20.

The rotating part 20 is provided to transport in a circular direction the cuvettes 152 received from the cuvette supplier 10, and a reagent containers (not shown in the drawings) accommodating reagent for coagulating specimen (blood sample). As shown in FIG. 2, the rotating part 20 is configured by a circular reagent table 21, annular reagent table 22 disposed on the outer side of the circular reagent table 21, annular secondary dispensing table 23 disposed on the outer side of the annular reagent table 22, and annular primary dispensing table 24 disposed on the outer side of the annular secondary dispensing table 23. The primary dispensing table 24, secondary dispensing table 23, and reagent tables 21 and 22 are configured so as to be mutually and independently rotatable in both clockwise and counter clockwise directions.

As shown in FIG. 2, the reagent tables 21 and 22 respectively include a plurality of holes 21a and 22a provided at predetermined spacing in the circumferential direction. The holes 21a and 22a of the reagent tables 21 and 22 are provided to load a plurality of reagent containers (not shown in the drawings) that hold reagent for coagulating the blood specimen. Furthermore, the primary dispensing table 24 and secondary dispensing table 23 respectively include a plurality of cylindrical holders 24a and 23a provided at predetermined spacing in the circumferential direction. The holders 24a and 23a are provided to hold the cuvettes 152 received from the cuvette supplier 10. A specimen contained in a test tube 150 of the transport device 3 is dispensed to a cuvette 152 held by the holder 24a of the primary dispensing table 24 in a primary dispensing process. Furthermore, a specimen contained in the cuvette 152 loaded in the primary dispensing table 24 is dispensed to a cuvette 152 loaded in the holder 23a of the secondary dispensing table 23 in a secondary dispensing process.

The specimen dispensing arm 30 functions to both aspirate specimen contained in a test tube 150 transported to the aspiration position 2a via the transport device 3, and dispensing the aspirated specimen into a cuvette 152 transported to the rotating part 20.

Figure 6:
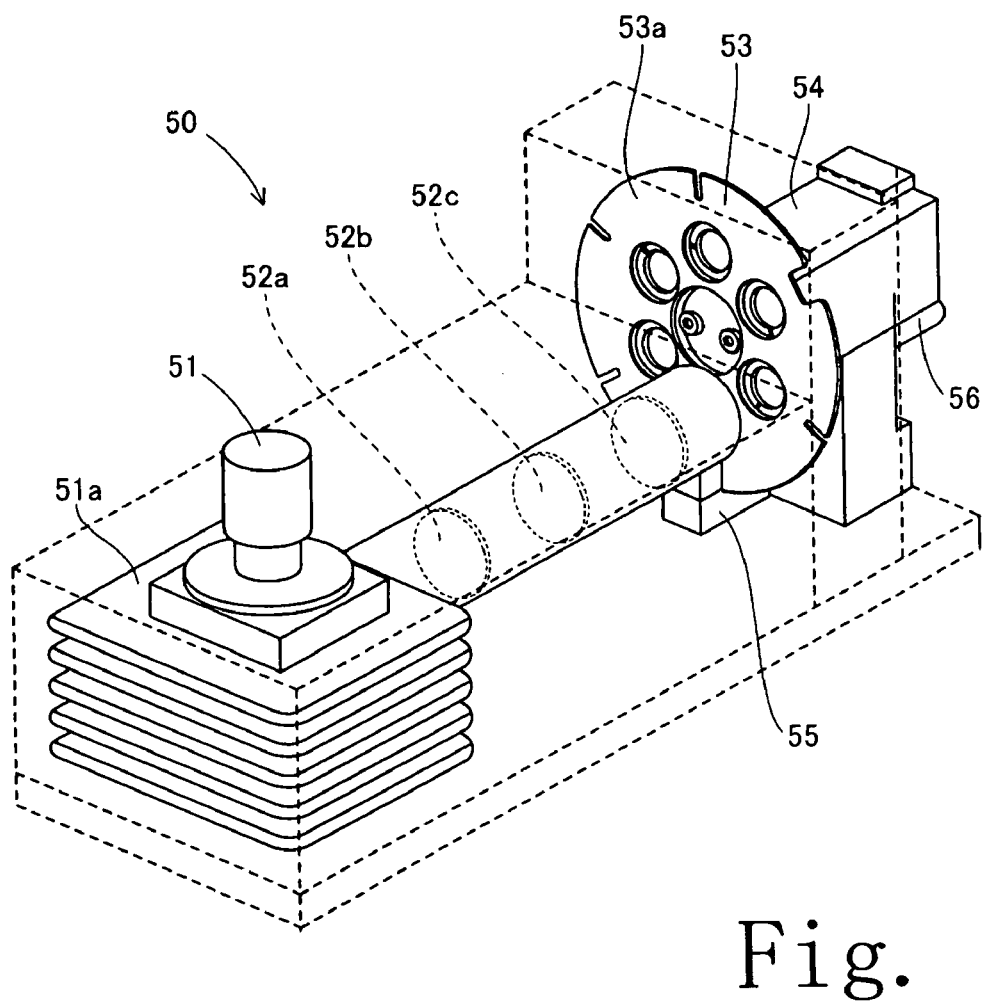
FIG. 6 is a perspective view of the lamp unit of the blood coagulation analyzer of the embodiment of FIG. 1.
Figure 7:
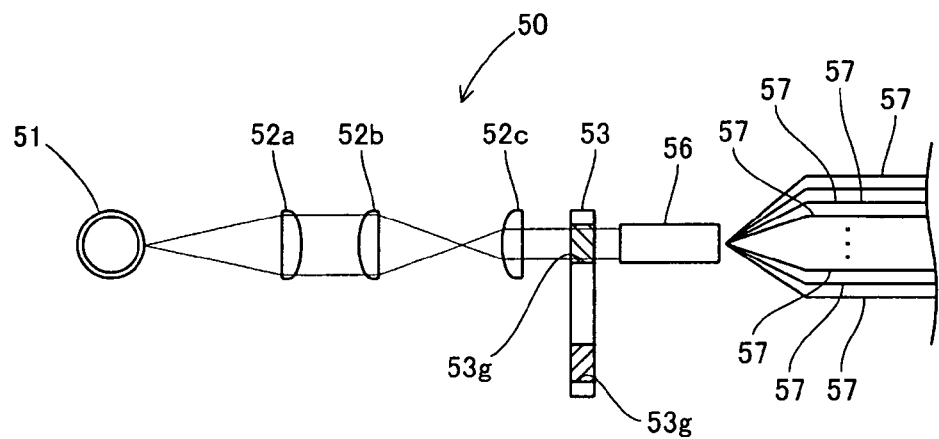
FIG. 7 is a schematic view showing the structure of the lamp unit of the blood coagulation analyzer of the embodiment of FIG. 1.

The lamp unit 50 is provided for supplying light used for photometry performed by the photometric part 80, as shown in FIG. 2. As shown in FIGS. 6 and 7, the lamp unit 50 is configured by a halogen lamp as a light source, collective lenses 52a through 52c, disk-shaped filter part 53, motor 54, transmission light sensor 55, optical fiber coupler 56, and eleven beam splitter optical fibers 57 (refer to FIG. 7).

As shown in FIG. 6, the halogen lamp 51 is accommodated in a lamp case 51a having a plurality of fins to dissipate the heat generated by the halogen lamp 51 via air cooling. The collective lenses 52a through 52c function to collect the light emitted from the halogen lamp 51. The collective lenses 52a through 52c are disposed on the optical path to guide the light emitted from the halogen lamp 51 to the optical fiber coupler 56. Furthermore, the light emitted from the halogen lamp 51 and collected by the collective lenses 52a through 52c is transmitted through one filter among the optical filters 53b through 53f of the filter part 53, which is described later.

Figure 8:
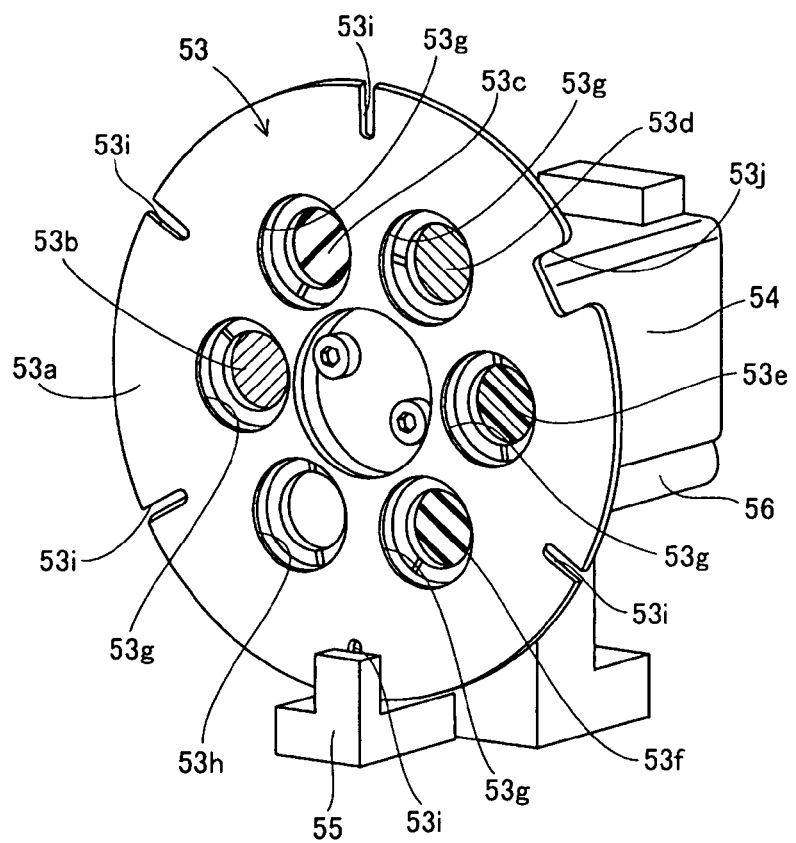
FIG. 8 is an enlarged perspective view of the filter part of the lamp unit shown in FIG. 6.

Furthermore, the filter part 53 of the lamp unit 50 is mounted on the motor shaft (not shown in the drawing) of the motor 54 so as to be rotatable, as shown in FIG. 8. The filter part 53 is provided with a filter plate 53a with five optical filters 53b through 53f that have respectively different light transmitting characteristics (transmission wavelengths). The filter plate 53a is provided with five holes 53g for mounting the optical filters 53b through 53f, and a hole 53h that can be blocked so as to not transmit light. The five holes 53g are respectively provided with five optical filters 53b, 53c, 53d, 53e, and 53f having respectively different light transmission characteristics (transmission wavelengths). The holes 53g and 53h are provided at predetermined angular intervals (equal spacing of 60 degrees in the present embodiment) in the direction of rotation of the filter part 53. The hole 53h is a reserve hole for installing an addition filter when necessary.

The optical filters 53b, 53c, 53d, 53e, and 53f transmit light at wavelengths of 340 nm, 405 nm, 575 nm, 660 nm, and 800 nm, respectively, and do not transmit light of different wavelength. Therefore, the optical filters 53b, 53c, 53d, 53e, and 53f have wavelength characteristics so as to transmit light at 340 nm, 405 nm, 575 nm, 660 nm, and 800 nm, respectively.

Furthermore, the filter plate 53a is provided with six slits at predetermined angular intervals (60 degree intervals in the present embodiment) in the circumferential direction. Five of the six slits are normal slits 53i, and the remaining slit is an origin point slit 53j. The origin point slit 53j is a large width slit in the direction of rotation of the filter plate 53a, whereas the other five normal slits 53i have smaller widths. The origin point slit 53j and normal slits 53i are formed at predetermined angular intervals (equal intervals of sixty degrees in the present embodiment) at intermediate angular positions between adjacent holes 53g and 53h.

Moreover, the filter part 53 is configured so as to continuously rotate when light is emitted from the lamp unit 50 to the cuvette 152 of the photometric part 80. Therefore, the five optical filters 53b through 53f having different light transmitting characteristics and the single blocked hole 53h (refer to FIG. 8) are sequentially arranged on the optical path of the light collected by the collective lenses 52a through 52c (refer to FIG. 7) in conjunction with the rotation of the filter plate 53a. Therefore, light of five different wavelengths are sequentially emitted.

Figure 3:
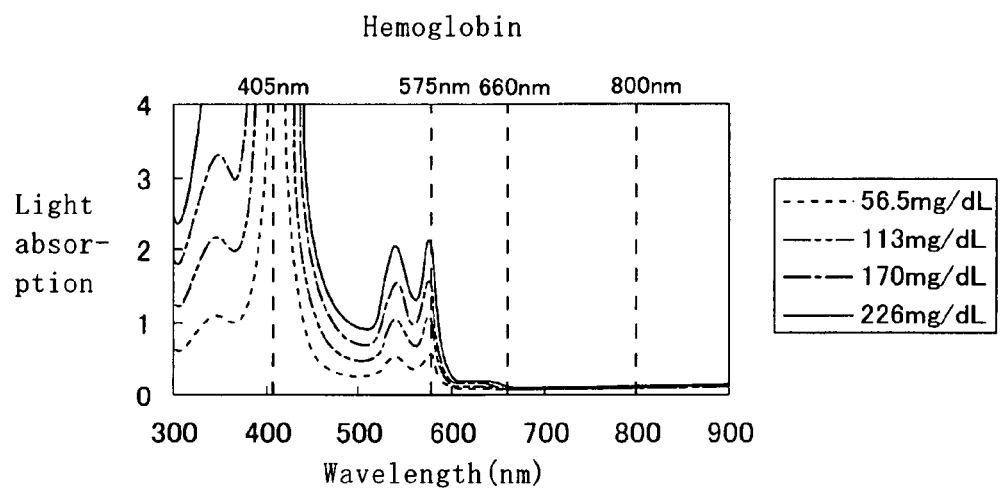
FIG. 3 is a graph showing the light absorption spectrum of an interference substance (hemoglobin)
Figure 4:
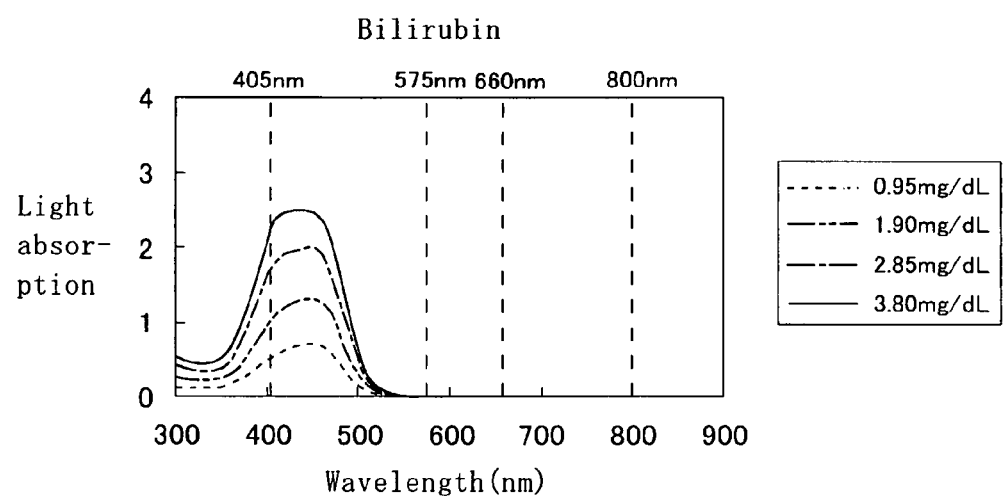
FIG. 4 is a graph showing the light absorption spectrum of an interference substance (bilirubin)
Figure 5:
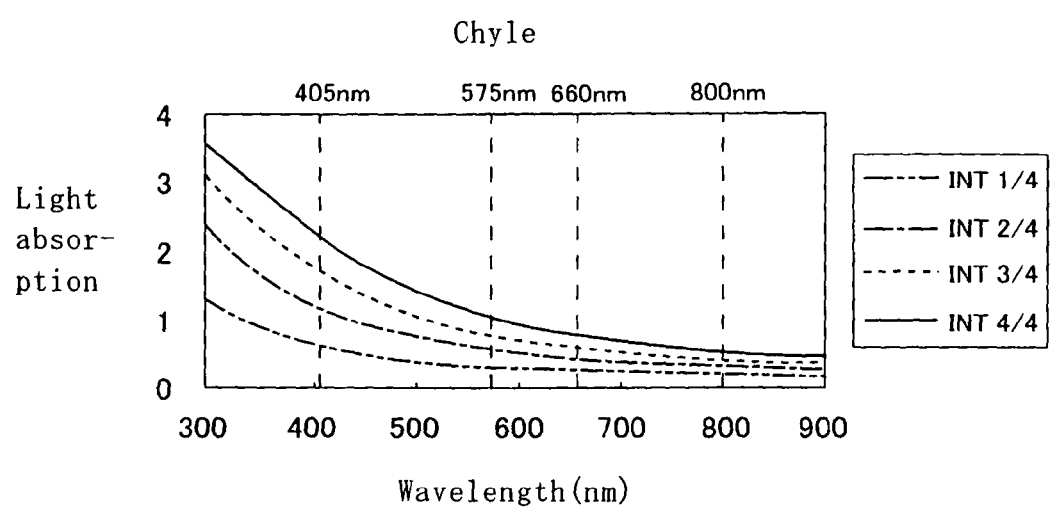
FIG. 5 is a graph showing the light absorption spectrum of another interference substance (chyle)

Light at a wavelength of 405 nm is absorbed by chyle, hemoglobin, and bilirubin, as shown in FIGS. 3 through 5. That is, chyle, hemoglobin, and bilirubin influence the photometric information measured using light at a wavelength of 405 nm. Furthermore, light at a wavelength of 575 nm is absorbed by chyle and hemoglobin, although essentially is not absorbed by bilirubin. That is, chyle and hemoglobin influence the photometric information measured using light at a wavelength of 575 nm. Light at wavelengths of 660 nm and 800 nm are absorbed by chyle, although essentially are not absorbed by bilirubin and hemoglobin. That is, chyle influences the photometric information measured using light at wavelengths of 660 nm and 800 nm. As shown in FIG. 5, chyle absorbed light from 405 nm in the low wavelength region to 800 nm in the high wavelength region, and chyle absorbed the more light at a wavelength of 660 nm than light at 800 nm. That is, chyle has less influence on photometric information measured using light at a wavelength of 800 nm than photometric information measured using light at 660 nm.

The transmission light sensor 55 is provided to detect the passage of light through the origin point slit 53j and normal slits 53i in conjunction with the rotation of the filter part 53, as shown in FIG. 8. The sensor 55 detects light from the light source through the slit via the light receiving unit as it passes through the origin point slit 53j and normal slits 53i, and outputs a detection signal. The detection signal output by the sensor 55 has a longer output time when light passes through the origin point slit 53*j* than the output signal when light passes through the normal slits 53*i* since the origin point slit 53*j* has a larger width than the normal slits 53*i*. Therefore, the filter part 53 can be monitored for normal rotation based on the detection signals from the sensor 55.

Figure 9:
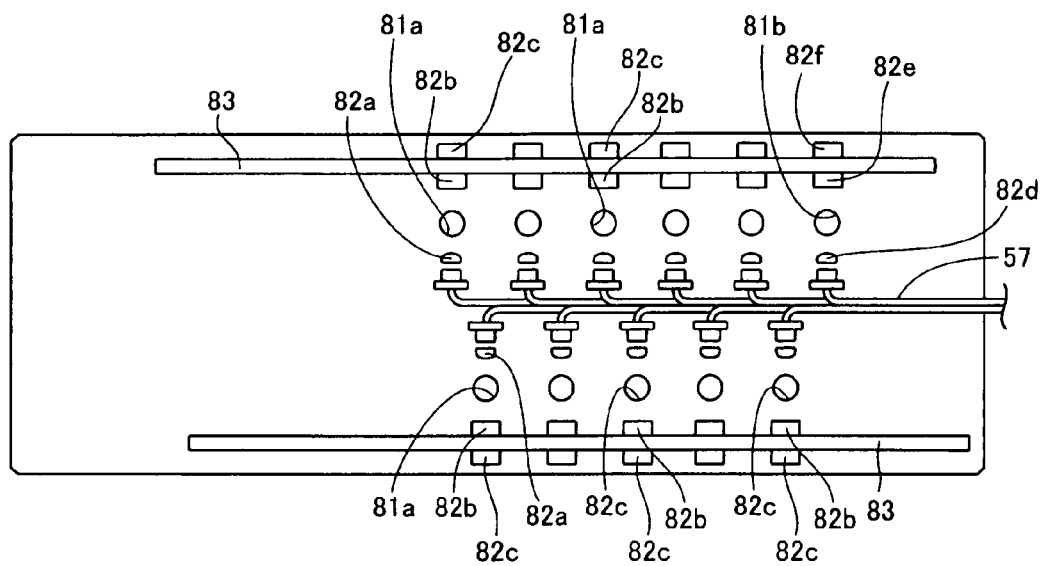
FIG. 9 briefly illustrates the internal structure of the detection part of the photometric part of the blood coagulation analyzer of the embodiment of FIG. 1.

The optical fiber coupler 56 functions to direct the light that has passed through the optical filters 53*b* through 53*f* to the respective eleven beam splitter optical fibers 57. That is, the optical fiber coupler 56 simultaneously guides light of like quality to the eleven beam splitter optical fibers 57. Furthermore, the leading ends of the eleven beam splitter optical fibers 57 are connected to the photometric part 80, and light from the lamp unit 50 is directed to the analysis sample within a cuvette 152 set in the photometric part 80, as shown in FIG. 2. Specifically, the eleven beam splitter optical fibers 57 are disposed so as to supply light to ten insertion holes 81*a* and one reference light measurement hole 81*b* which are parts of the photometric part 80 described later, as shown in FIG. 9. Therefore, five kinds of light having different wavelength characteristics consecutively passes through the optical filters 53*b* through 53*f*, and is supplied to the photometric part 80 via the beam splitter optical fibers 57.

As shown in FIGS. 1 and 2, the reagent dispensing arm 60 is provided to mix reagent with the specimen in the cuvette 152 by dispensing the reagent within a reagent container (not shown in the drawings) loaded on the rotating part 20 into a cuvette 152 held in the rotating part 20. Thus, an analysis sample is prepared by adding reagent to the specimen. The cuvette transporter 70 is provided to transport the cuvette 152 between the rotating part 20 and the photometric part 80. In the present embodiment, the photometric part 80 is provided to heat the analysis sample prepared by adding reagent to the specimen, and over time receive the light from the analysis sample that has been illuminated by light of a plurality of wavelengths via the lamp unit 50, and measure the amount of transmitted light at a plurality of moments for each wavelength. Specifically, the photometric part 80 measures the amount of transmitted light over a time course using three types of light (405 nm, 660 nm, 800 nm) among five types of light (340 nm, 405 nm, 575 nm, 660 nm, and 800 nm) emitted from the lamp unit 50.

As shown in FIG. 2, the photometric part 80 is configured by a cuvette loader 81, and detection unit 82 disposed below the cuvette loader 81. The cuvette loader 81 is provided with ten insertion holes 81*a* for inserting cuvettes 152 (refer to FIG. 2), and a single reference light measurement hole 81*b* for measuring a reference light and in which a cuvette is not inserted. The cuvette loader 81 has a built-in heating device (not shown in the drawing) for heating a cuvette 152 loaded in the insertion holes 81*a* to a predetermined temperature. The reference light measurement hole 81*b* is provided for monitoring the characteristics of the light emitted from the beam splitter optical fibers 57. Specifically, characteristics such as fluctuation and the like originating in the halogen lamp 51 of the lamp unit 50 are detected as electrical signals by directly receiving the light emitted by the beam splitting optical fibers 57 via a reference light photoelectric conversion element 82*e* of the detection unit 82. Signals corresponding to the transmission light of the analysis sample are corrected by subtracting the characteristics of the detected light from the signals corresponding to the transmission light of the analysis sample within the cuvette 152 inserted in the insertion hole 81*a*. Thus, it is possible to suppress minute differences caused by the characteristics of the light in each photometric measurement.

Figure 10:
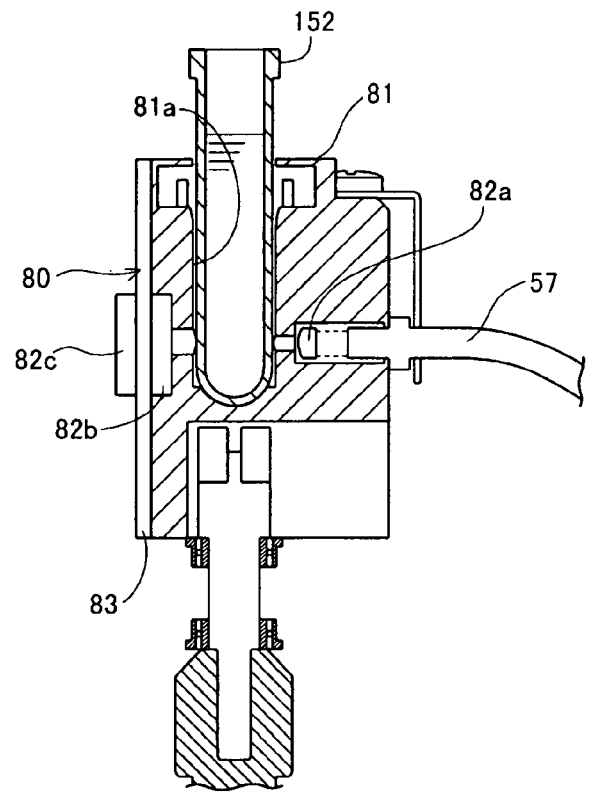
FIG. 10 is a cross section view illustrating the structure of the detection part of the photometric part of the blood coagulation analyzer of the embodiment of FIG. 1.

The detection part 82 of the photometric part 80 is configured so as to be capable of performing photometric measurements under a plurality of conditions on an analysis sample within a cuvette 152 inserted in the insertion hole 81*a*. As shown in FIGS. 9 and 10, the detection part 82 is provided with a collimator lens 82*a*, photoelectric conversion element 82*b*, and preamp 82*c* corresponding to each insertion hole 81*a* in which a cuvette 152 is inserted, and a reference light collimator lens 82*d*, reference light photoelectric conversion element 82*e*, and reference light preamp 82*f* corresponding to the reference light measurement hole 81*b* (refer to FIG. 1).

As shown in FIGS. 9 and 10, the collimator lens 82*a* is disposed between the end of the beam splitter optical fiber 57 that guides the light emitted from the lamp unit 50, and the corresponding insertion hole 81*a*. The collimator lens 82*a* is provided to render the light beams emitted from the beam splitter optical fiber 57 in parallel rays. The photoelectric conversion element 82*b* is mounted on the surface on the insertion hole 81*a* side of the baseplate 83 so as to face the end of the beam splitter optical fiber 57 with the insertion hole 81*a* therebetween. The photoelectric conversion element 82*b* functions to detect the light transmitted through the analysis sample (hereafter referred to as "transmission light") when light irradiates the analysis sample within the cuvette 152 inserted in the insertion hole 81*a*, and outputs electric signals (analog signals) corresponding to the detected transmission light. The photoelectric conversion element 82*b* is disposed so as to receive five kinds of light emitted from the beam splitter optical fiber 57 of the lamp unit 50.

The preamp 82*c* is mounted on the opposite surface of the baseplate 83 relative to the insertion hole 81*a* so as to amplify the electric signal (analog signal) output from the photoelectric conversion element 82*b*.

Figure 11:
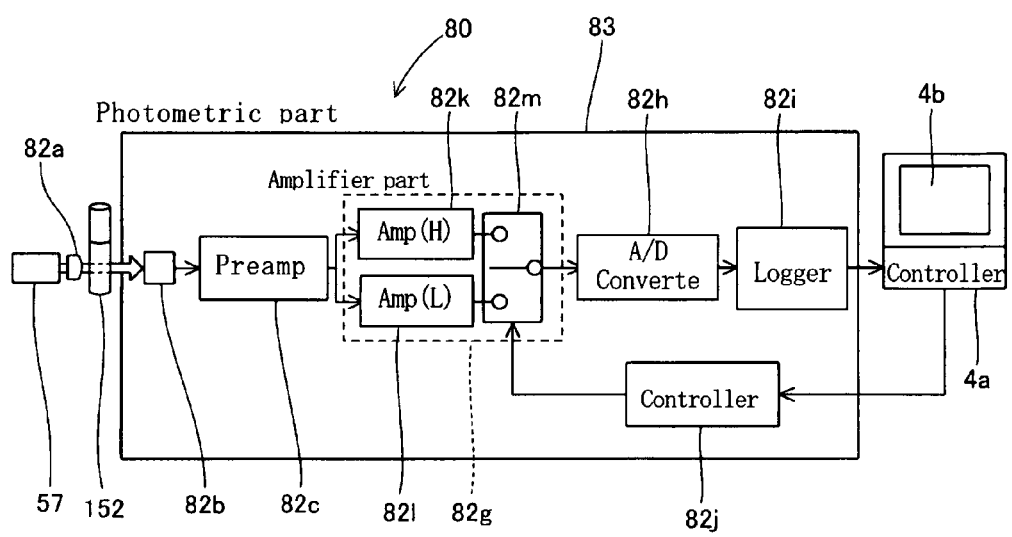
FIG. 11 is a block diagram of the photometric part of the blood coagulation analyzer of the embodiment of FIG. 1.

As shown in FIG. 11, the baseplate 83 is provided with the photoelectric conversion elements 82*b* (reference light photoelectric conversion element 82*e*), preamps 82*c* (reference light preamp 82*f*), as well as amplifier part 82*g*, A/D converter 82*h*, logger 82*i*, and controller 82*j*. The amplifier 82*g* includes amp (L) 82*k* with a predetermined gain (amplification factor), amp (H) 82*l* with a gain (amplification factor) higher than the amp (L) 82*k*, and switch 82*m*. In the present embodiment, an electric signal from the preamp 82*c* is input to both the amp (L) 82*k* and amp (H) 82*l*. The amp (L) 82*k* and amp (H) 82*l* are provided to further amplify the electric signals from the preamps 82*c*. The switch 82*m* is provided to selectively either output the electric signals from the amp (L) 82*k* to the A/D converter 82*h*, or output the electric signal from the amp (H) 82*l* to the A/D converter 82*h*. The switch 82*m* is configured so as to perform a switching operation via the input of control signals from the controller 82*j*.

The A/D converter 82*h* is provided to convert the electric signals (analog signals) from the amplifier part 82*g* to digital signals. The logger 82*i* functions to temporarily save the digital signal data (photometric information) from the A/D converter 82*h*. The logger 82*i* is electrically connected to the controller 4*a* of the control device 4, and sends the digital signal data obtained in the photometric part 80 to the controller 4*a* of the control device 4.

As shown in FIGS. 1 and 2, the rush specimen acceptor 90 is provided to perform a sample analysis process on sample requiring immediate processing. The rush sample acceptor 90 is capable of performing an interrupt on behalf of a rush specimen when there is an on-going specimen analysis process being performed on a specimen supplied from the transport device 3. The cuvette disposal 100 is provided to dispose of cuvettes 152 from the rotating part 20. As shown in FIG. 2, the cuvette disposal 100 is configured by a cuvette waste part 101, disposal hole 102 provided at predetermined spacing from the cuvette waste part 101 (refer to FIG. 1), and waste box 103 provided below the disposal hole 102. The cuvette waste part 101 is provided to move a cuvette 152 from the rotating part 20 to the waste box 103 via the disposal hole 102 (refer to FIG. 1). A fluid provider 110 is provided to supply a fluid such as cleaning liquid to a nozzle provided on each dispensing arm during the shutdown process of the blood coagulation analyzer 1.

The control device 4 is configured by a personal computer 401, and includes a controller 4a that includes a CPU, ROM, RAM and the like, a display 4b, and a keyboard 4c, as shown in FIG. 1. The display 4b is provided to display information relating to interference substances (hemoglobin, chyle (lipids), and bilirubin) present in the specimen, and analysis results (coagulation time) obtained by analyzing the digital signal data received from the photometric part 80.

Figure 12:
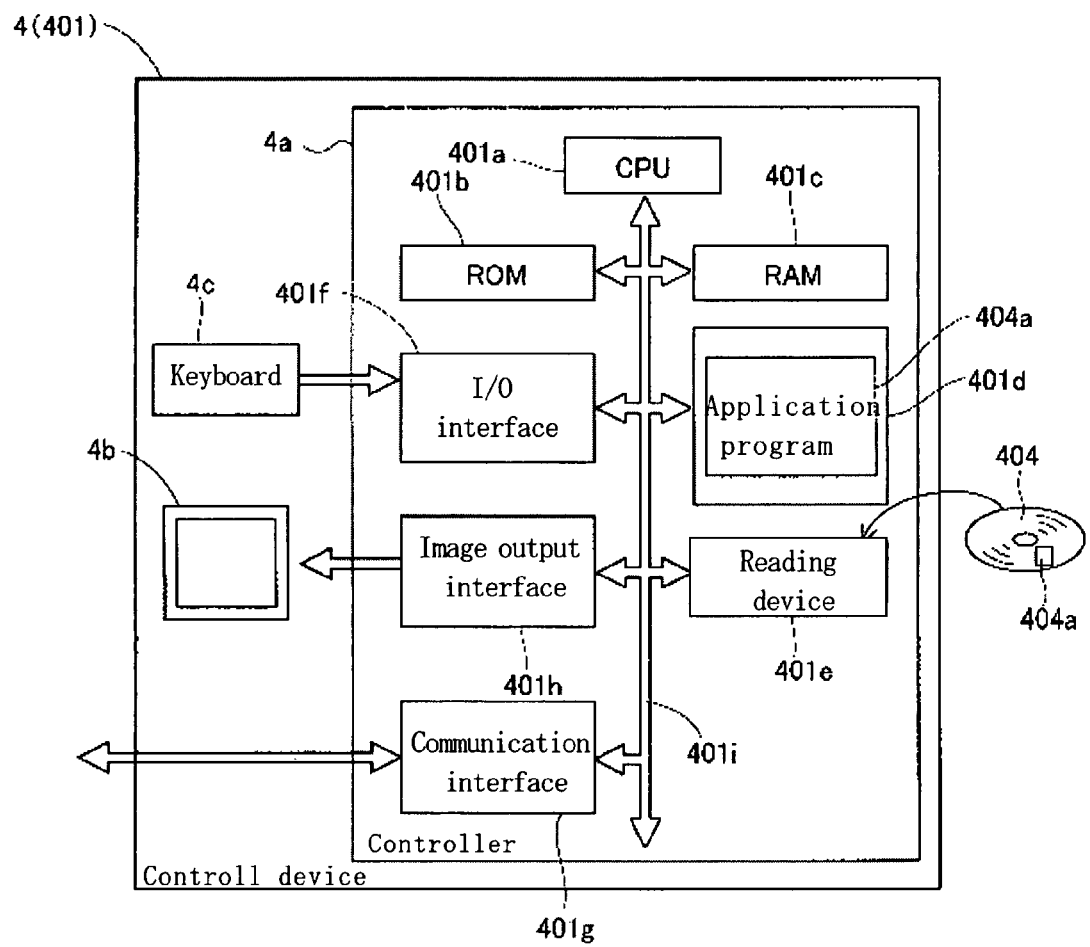
FIG. 12 is a block diagram of the control device of the blood coagulation analyzer of the embodiment of FIG. 1.

The structure of the control device 4 is described below. As shown in FIG. 12, the controller 4a is mainly configured by a CPU 401a, ROM 401b, RAM 401c, hard disk 401d, reading device 401e, I/O interface 401f, communication interface 401g, image output interface 401h. The CPU 401a, ROM 401b, RAM 401c, hard disk 401d, reading device 401e, I/O interface 401f, communication interface 401g, image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401a when these computer programs are being executed. The hard disk 401d contains various installed computer programs to be executed by the CPU 401a such as an operating system and application programs and the like, and data used in the execution of these computer programs. Also installed on the hard disk 401d is the application program 404a used for blood coagulation time measurement of the present embodiment.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a used for blood coagulation time measurement; the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over an electric communication line by means of the electric communication line (wire line or wireless). For example, the application program 404a may be stored on the hard disk of a server computer connected to the internet, such that the computer 401a can access the server computer and download the application program 404a, and then install the application program 404a on the hard disk 401d.

Also installed on the hard disk 401d is an operating system providing a graphical user interface, such as, for example, Windows® of Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user can input data in the computer 401 using the keyboard 4c.

The communication interface 401g is, for example, and Ethernet® interface. The computer 401 can send and receive data to and from the detection device 2 using a predetermined communication protocol via the communication interface 401g.

The image output interface 401h is connected to the display 4b configured by an LCD, CRT or the like, such that image signals corresponding to the image data received from the CPU 401a can be output to the display 4b. The display 4b displays an image (screen) in accordance with the input image signals.

In the present embodiment, the application program 404a for blood coagulation time measurement installed on the hard disk 401d of the control device 4a analyzes the coagulation time of analysis samples based on the amount of transmission light (digital signal data) of the analysis sample obtained by the photometric part 80 of the detection device 2. The blood coagulation time is the time from the moment the blood coagulation reagent is added to a specimen in a cuvette 152 until the analysis sample with the added reagent loses flowability (coagulation time). The coagulation reaction in which the analysis sample loses flowability is a reaction that changes fibrinogen within the specimen to fibrin via the added reagent. In the blood coagulation analyzer 1 of the present embodiment, the coagulation time of the reaction dependent on the amount of fibrinogen within the specimen is measured by the amount of change of the transmission light of the analysis sample (the difference between the amount of transmission light before the reaction and the amount of transmission light after the reaction), as shown in FIGS. 13 and 14.

Figure 13:
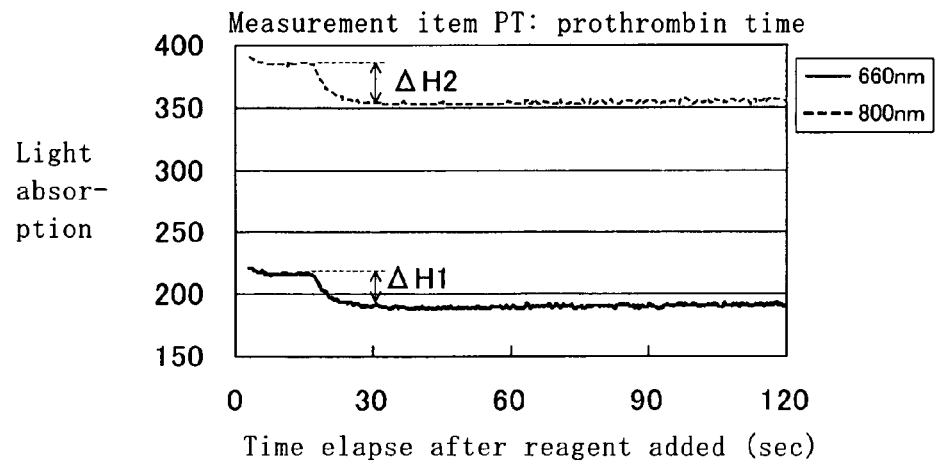
FIG. 13 shows the measurement results of a specimen contaminated by interference substances measured by the photometric part of the blood coagulation analyzer of the embodiment of FIG. 1.
Figure 14:
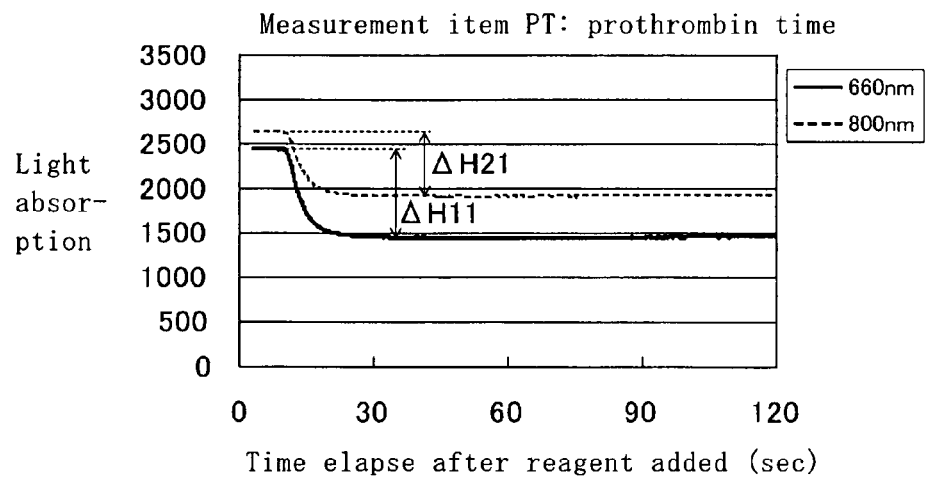
FIG. 14 shows the measurement results of a normal specimen measured by the photometric part of the blood coagulation analyzer of the embodiment of FIG. 1.

When a sample containing interference substances (chyle) was measured in the blood coagulation analyzer 1 of the present embodiment, the measurement results measured at the low wavelength side of 660 nm were reduced by the influence of the interference substance (chyle), and the amount of transmission light was approximately 190 to 220, as shown in FIG. 13. When a wavelength of 660 nm was used, the change ΔH1 of the amount of transmission light representing a blood coagulation reaction (the difference between the amount of transmission light before the reaction and the amount of transmission light after the reaction) also tended to be reduced by the influenced of interference substance (chyle). In contrast, measurement results measured on the high wavelength side at 800 nm were not as influenced by interference substances, and were higher than the amount of transmission light measured at 660 nm (approximately 190 to 220) at approximately 350 to 390. When a wavelength of 800 m was used, the change ΔH2 of the transmission light representing a blood coagulation reaction (>ΔH1) is also not as influenced by the interference substance (chyle), and was not easily reduced. Therefore, when measuring specimens containing interference substances (chyle), performing the measurement at a wavelength of 800 nm in the high wavelength region captures a greater change in the amount of transmission light via the coagulation reaction than measurement at a wavelength of 660 nm in the low wavelength region.

When a normal sample that did not contain interference substances was measured, the change ΔH11 in the amount of transmission light measured at a low wavelength of 660 nm (ΔH11=approximately 980 (=transmission light before reaction (about 2440)−transmission light after reaction (about 1460)) was greater than the change ΔH21 in the amount of transmission light measured at a high wavelength of 800 nm (ΔH21=approximately 720 (=transmission light before reaction (about 2630)−transmission light after reaction (about 1910)). Therefore, when measuring normal samples, measurement at a low wavelength 660 nm captures a greater change in the amount of transmission light via the reaction than measurement at a wavelength of 800 nm in the high wavelength region.

Figure 15:
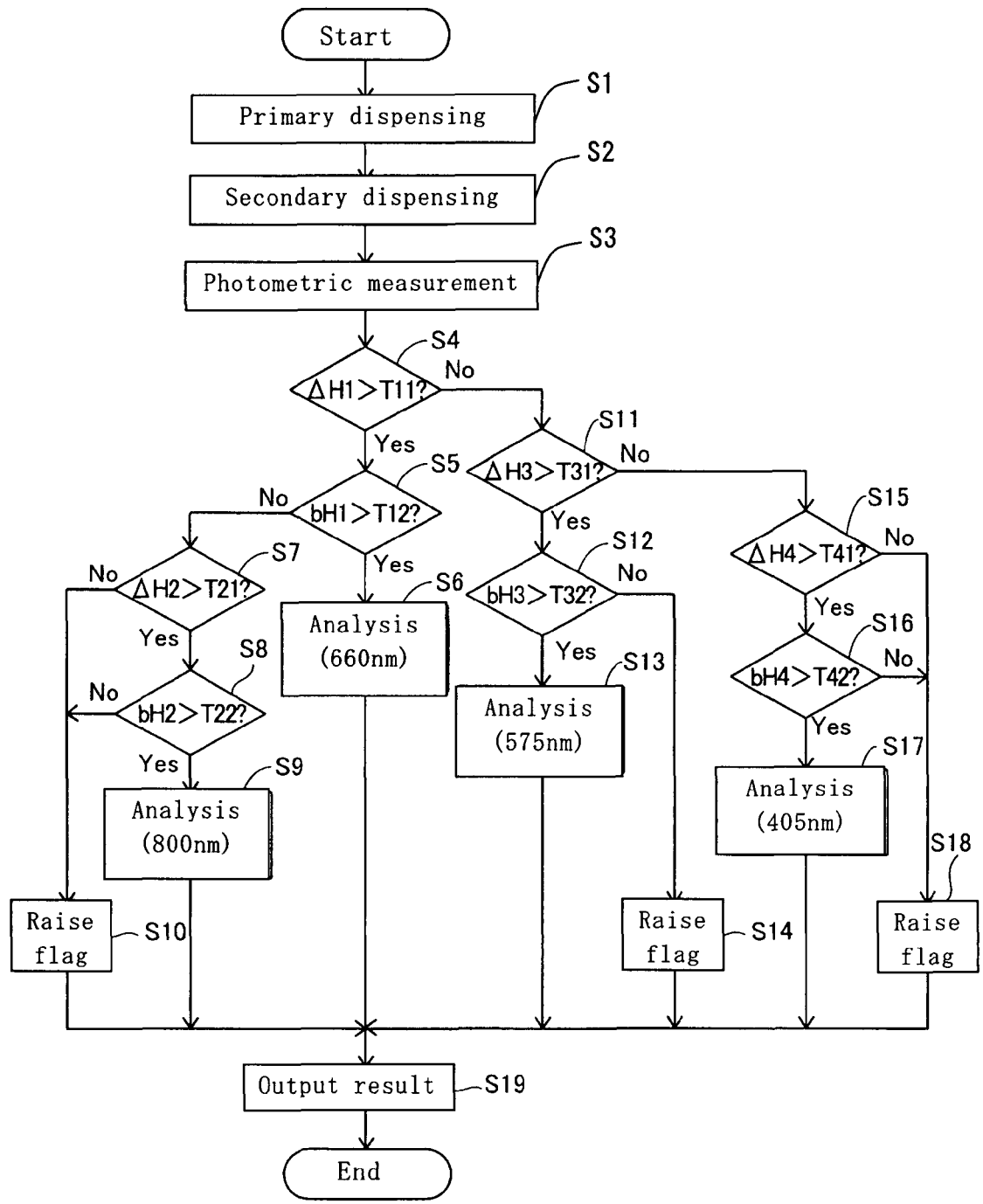
FIG. 15 is a flow chart showing the sequence of the specimen analysis operation of the blood coagulation analyzer of the embodiment of FIG. 1.

FIG. 15 is a flow chart showing the sequence of the specimen analysis operation of the blood coagulation analyzer of the embodiment of FIG. 1. The specimen analysis operation performed by the blood coagulation analyzer 1 is described in detail below with reference to FIGS. 1, 2, 8, 10, 11, and 15.

First, the blood coagulation analyzer 1 is initialized by turning ON the power sources of the detection device 2 and control device 4 of the blood coagulation analyzer 1 shown in FIG. 1. In this way, an operation is performed to return each dispensing arm and the mechanism that moves the cuvettes 152 to the initial positions, and software stored in the controller 4a of the control device 4 is initialized.

Then, the rack 151 loaded with test tubes 150 containing specimens is transported by the transport device shown in FIG. 2. Thus, the rack 151 is transported from the rack set region 3a to a position corresponding to the aspirating position 2a of the detection device 2.

In step S1, a predetermined amount of specimen is aspirated from the test tube 150 via the specimen dispensing arm 30 (refer to FIG. 2). The specimen dispensing arm 30 is then moved above the cuvette 152 held on the primary dispensing table 24 of the rotating part 20. Thereafter, the sample within the cuvette 152 is allocated by discharging the sample from the specimen dispensing arm 30 into the cuvette 152 of the primary dispensing table 24.

In step S2, a predetermined amount of specimen is aspirated from the cuvette 152 held in the holder 24a of the primary dispensing arm 24 via the specimen dispensing arm 30. Thereafter, the secondary dispensing process is performed by discharging predetermined amounts of specimen from the dispensing arm 30 to a plurality of cuvettes 152 on the secondary dispensing table 23. Then, the reagent dispensing arm 60 is actuated, and blood coagulation reagent within a reagent container (not shown in the drawing) which is loaded in the reagent tables 21 and 22 is added to the specimen within the cuvettes 152 on the secondary dispensing table 23. Thus, analysis samples are prepared. Then, the cuvette transporter 70 moves the cuvette 152 containing the analysis sample from the secondary dispensing table 23 to the insertion hole 81a of the cuvette loader 81 of the photometric part 80.

In step S3, a plurality (ten types) of transmission light are obtained from the analysis sample by photometric measurement of the analysis sample within the cuvette 152 under a plurality of conditions via the detection part 82 of the photometric part 80. Specifically, the cuvette 152 inserted in the insertion hole 81a of the cuvette loader 81 is first heated to a predetermined temperature by a heating device (not shown in the drawing). Thereafter, light is emitted from the beam splitter optical fiber 57 of the lamp unit 50 and irradiates the cuvette 152 on the cuvette loader 81, as shown in FIG. 10. Light of five different wavelengths (340 nm, 405 nm, 575 nm, 660 nm, 800 nm) emitted from the beam splitter optical fiber 57 periodically illuminates via the rotation of the filter part 53 (refer to FIG. 8). The light of each wavelength emitted that is emitted from the beam splitter optical fiber 57 and passes through the cuvette 152 and the analysis sample within the cuvette 152 is sequentially detected by the photoelectric conversion element 82b. Then, the electric signals, which represent the amount of transmission light corresponding to the light of five different wavelengths that have been converted by the photoelectric conversion element 82b, are amplified by the preamp 82c and sequentially input to the amplifier 82g.

In the amplifier part 82g, the electric signals, which represent the amount of transmission light corresponding to the light of five different wavelengths output from the preamp 82c (refer to FIG. 11), are input to the high amplification factor amp (H) 82l and normal amplification factor amp (L) 82k. The controller 82j controls the switch 82m so as to output the electric signals that have been amplified by the amp (H) 82l are output to the A/D converter 82h, and thereafter the electric signals that have been amplified by the amp (L) 82k are output to the A/D converter 82h. The switch 82m repeatedly switches in accordance with the timing of the rotation of the filter part 53 (refer to FIG. 8) in the lamp unit 50. Thus, the electrical signals representing the transmission light corresponding to the light at five different wavelengths are respectively amplified by two different amplification factors in the amplifier part 82g, and a total of ten electric signals are repeatedly output to the A/D converter 82h. These ten electric signals are converter to digital signals by the A/D converter 82h and the digital signals are temporarily stored in the logger 82l, and subsequently these digital signals are sequentially transmitted to the controller 4a of the control device 4. Thus, the acquisition of a plurality (ten types) of transmission light data for an analysis sample is completed by the photometric part 80. The amount of change at each wavelength (=amount of transmission light before reaction−amount of transmission light after reaction) is calculated from the received transmission light data by the controller 4a of the control device 4. The obtained transmission light data are then stored in the RAM 401c of the control device 4.

In the present embodiment, after the transmission light data is obtained by the photometric part 80 in step S3, a determination is made in step S4 as to whether or not the change (ΔH1) of the amount of transmission light of the analysis sample measured at a wavelength of 660 nm is greater than a threshold value (T11). The blood coagulation react induces an optical change in the analysis sample, and this optical change is represented as a change in the amount of transmission light. Therefore, when there is a large change in amount of transmission light, it may be considered indicative of a large optical change in the analysis sample caused by the blood coagulation reaction. The coagulation time can be measured with high precision using the large change in the amount of transmission light over time due to the large S/N ratio of the transmission light data.

When the change ΔH1 of the transmission light measured at 660 nm is greater than the threshold value (T11) in step S4, a determination is made in step S5 as to whether or not the amount of transmission light (bH1) at 660 nm at the lag phase (the time from the initial preparation of the measurement sample to before the measurement sample is optically changed by the blood coagulation reaction) is greater than a predetermined threshold value (T12). The coagulation reaction starts blood coagulation by changing the fibrinogen in the plasma to fibrin through many internal and external reaction systems. That is, blood coagulation does not soon start even though blood coagulation reagent is mixed with the plasma, rather a coagulation reaction normally starts after approximately seven seconds in external systems (PT measurement reagent), and normally after about 14 seconds in internal systems (APTT measurement reagent). Accordingly, the optical information at time point before the coagulation reaction is indicated (lag phase) is optical information representing conditions before an optical change has occurred via the coagulation reaction, and is identical to the optical information obtained from a diluted specimen to which blood coagulation reagent has not been added. Therefore, whether or not the transmission light data is usable for analysis can be determined by comparing the threshold value (T12) and the amount of transmission light (bH1) in the lag phase of a specimen diluted with reagent used for blood coagulation time measurement. When an analysis sample contains substantial interference substances, very little received light is detected by the photoelectric conversion element 82b of the photometric part 80, and the amount of transmission light is reduced in the lag phase. Thus, when the amount of transmission light (bH1) at 660 μm is less than the threshold value (T12) in the lag phase, the interference substances greatly influence the amount of transmission light at this wavelength (660 nm) obtained by the photometric part 80, and is determined that the data are not usable for analysis. The transmission light data during the lag phase is obtained using the data from the start of photometric measurement until a predetermined time has elapsed. Furthermore, the determination is not limited to this method inasmuch as the change in the amount of transmission light over time may be analyzed to determine the lag phase, and the transmission light data of this period may be used so as to differentiate the amount of transmission light and determine the degree of change of transmission light, and set the lag phase as the time from the start of photometric measurement until the differential value exceeds a predetermined value.

When the amount of transmission light (bH1) at 660 nm in the lag phase is greater than the threshold value (T12) in step S5, the analysis item (for example, "PT") coagulation time is determined in step S6 by the CPU 401a of the control device 4 analyzing the transmission light data of the analysis sample measured at 660 nm from among the plurality of transmission light data measured by the photometric part 80. Thereafter, the controller 4a output the analysis results such as coagulation time and the like.

When the amount of transmission light (bH1) at 660 nm in the lag phase is less than the threshold value (T12) in step S5, however, a determination is made in step S7 as to whether or not the change (ΔH2) in the amount of transmission light of the analysis sample measured at 800 nm exceeds a threshold value (T21). That is, in this case the transmission light data at 660 nm is greatly affected by the interference substances, and since these data can not be used for analysis a determination is made as to whether or not the transmission light data at 800 nm which were not much influenced by interferences substances are usable for analysis. When the change (ΔH2) in the amount of transmission light at 800 nm is greater than a threshold value (T21) in step S7, then a determination is made in step S8 as to whether or not the transmission light (bH2) at 800 nm in the lag phase exceeds a predetermined threshold value (T22). When the transmission light (bH2) at 800 nm in the lag phase exceeds the threshold value (T22), analysis is performed using the 800 nm transmission light data. That is, in step S9, the coagulation time of the analysis item is determined by the CPU 401a of the control device 4 analyzing the transmission light data of the analysis sample measured at 800 nm from among the plurality of transmission light data measured by the photometric part 80. Thereafter, the controller 4a output the analysis results such as coagulation time and the like. When the transmission light (bH2) at 800 nm in the lag phase is less than the threshold value (T22) in step S8, the CPU 401a does not execute analysis, and a measurement error flag is raised in the measurement results in step S10. Furthermore, since the 800 nm transmission light data, which are least affected by interference substances among all measurement wavelengths, are determined to be unusable for analysis even when the change (ΔH2) of the amount of transmission light at 800 nm is below the threshold value (T21) in step S7, and the CPU does not perform analysis and a measurement error flag is raised in the measurement results in step S110.

When the change (ΔH1) in the amount of transmission light measured at 660 nm is less than a threshold value (T11) in step S4, a determination is made in step S11 as to whether or not the change (ΔH3) of the amount of transmission light of the analysis sample measured at 575 nm is greater than a threshold value (T31). In this case, a determination is made as to whether or not the 575 nm transmission light data, which has higher measurement sensitivity, is usable for analysis since the change in the amount of 660 nm transmission light is inadequate.

When the change (ΔH3) in the amount of transmission light at 575 nm is greater than a threshold value (T31) in step S11, then a determination is made in step S12 as to whether or not the transmission light (bH3) at 575 nm in the lag phase exceeds a predetermined threshold value (T32). When the 575 nm transmission light (bH3) is greater than the threshold value (T32), then in step S13 the CPU 401a of the control device 4 analyzes the transmission light data of the analysis sample measured at 575 nm from among the plurality of transmission light data measured by the photometric part 80, and determines the coagulation time of analysis item. Thereafter, the controller 4a output the analysis results such as coagulation time and the like. When the transmission light (bH3) at 575 nm in the lag phase is less than the threshold value (T32) in step S12, the CPU 401a does not execute analysis, and a measurement error flag is raised in the measurement results in step S14.

When the change (ΔH3) in the amount of transmission light measured at 575 nm is less than a threshold value (T31) in step S11, a determination is made in step S15 as to whether or not the change (ΔH4) of the amount of transmission light of the analysis sample measured at 405 nm is greater than a threshold value (T41). In this case, a determination is made as to whether or not the 405 nm transmission light data, which has higher measurement sensitivity, is usable for analysis since the change in the amount of 575 nm transmission light is inadequate.

When the change (ΔH4) in the amount of transmission light at 405 nm is greater than a threshold value (T41) in step S15, then a determination is made in step S16 as to whether or not the transmission light (bH4) at 405 nm in the lag phase exceeds a predetermined threshold value (T42). When the 405 nm transmission light (bH4) is greater than the threshold value (T42), then in step S17 the CPU 401a of the control device 4 analyzes the transmission light data of the analysis sample measured at 405 nm from among the plurality of transmission light data measured by the photometric part 80, and determines the analysis item coagulation time. Thereafter, the controller 4a output the analysis results such as coagulation time and the like. When the transmission light (bH4) at 405 nm in the lag phase is less than the threshold value (T42) in step S16, the CPU 401a does not execute analysis, and a measurement error flag is raised in the measurement results in step S18. Furthermore, the CPU 401a does not execute analysis and a measurement error flag is raised in the measurement results in step S18 even when the change (ΔH4) of the amount of transmission light measured at 405 nm is less than the threshold value (T41) in step S15.

After completion of analyses by the CPU 401a of the control device 4 in steps S6, S9, S13, and S17, the analysis results such as coagulation time and the like obtained in steps S6, S9, S13, and S17 are displayed on the display 4b of the control device 4 in step S19. When a measurement error flag is attached to the measurement results in step S10, S14, or S18, "measurement error" is displayed together with an error code on the display 4b of the control device 4. Thus, a user is made aware of the error content via the error code displayed on the display 4b and refers to the error code in a technical manual. In this way the specimen analysis operation is completed by the blood coagulation analyzer 1.

In the present embodiment, a suitable measurement wavelength can be selected for each specimen, and high precision analysis can be performed on each specimen. That is, the wavelength used for analysis can be changed based on the change over time in the amount of transmission light, which changes in accordance with the progress of the blood coagulation reaction by selecting a wavelength to be used in the analysis based on the change (ΔH1 through ΔH4) in the amount of transmission light over a time course obtained by the photometric part 80. Thus, a change in the amount of transmission light over time can be obtained which is scarcely affected by interference substances if a long wavelength is selected that is not readily absorbed by the interference substances contained in the specimen when it is found that an interference substance (chyle) influences the change in the amount of transmission light over time obtained by the photometric part 80. As a result, the control device 4 can accurately analyze the coagulation time of a blood sample since the change in the amount of transmission light over time that is unaffected by interference substances is captured as a change induced in blood by the coagulation reaction.

In the present embodiment, the transmission light of an analysis sample is measured in the lag phase at wavelengths of 800 nm, 660 nm, 575 nm, and 405 nm and compared to threshold values to determine whether or not the transmission light is within the analysis range of the control device 4, and when the lag phase transmission light exceeds the analysis range of the control device 4, the selected wavelength can be changed so as to select lag phase transmission light that is within the analysis range of the control device 4. As a result, the control device 4 can perform accurate analysis since the analysis is not performed using low reliability transmission light that exceeds the analysis range.

In the present embodiment, when accurate analysis can not be performed using data at a specific wavelength (for example 660 nm), data at another wavelength (for example, 800 nm) can be selected to perform accurate analysis because the configuration allows the selection of the wavelength used in the analysis in which transmission light data (amount of light received over time) are used for blood coagulation analysis. Furthermore, a first wavelength data may be used preferentially since a prioritized determination is made as to whether or not a first wavelength (660 nm) data, which are scarcely affected by interference substances and can be obtained with suitable measurement sensitivity, can be used for analysis. The first wavelength data is less affected by interference substances than data of a second wavelength (575 nm, 405 nm) that is shorter than the first wavelength. Furthermore, the first wavelength data is obtained with higher resolution than that of a third wavelength (800 nm) that is longer than the first wavelength. Therefore, it is verified that the first wavelength data are highly reliable. When an optical change in the analysis sample caused by the coagulation reaction can not be captured as an adequately large change in transmission light among the data at the first wavelength, it is possible to perform more accurate analysis by selecting data of a second wavelength (575 nm, 405 nm). When the second wavelength is unusable for analysis, the analysis is suspended or another wavelength can be selected. Moreover, when measurement is greatly affected by interference substances in the specimen, a third wavelength (800 nm) may be selected so as to use data obtained at the third wavelength, which is scarcely affected by the interference substance, for the analysis. When the third wavelength is unusable for analysis, the analysis is suspended or another wavelength can be selected. According to this configuration, a separate structure for optically measuring interference substances becomes unnecessary, thus rendering the apparatus more compact and lowering costs.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

For example, the present embodiment has been described in terms of a configuration for selecting a wavelength to be used in analysis using the transmission light of the lag phase, and the change in the amount of transmission light at each wavelength. However, the present invention is not limited to this configuration. The wavelength used in the analysis may be selected using just the change in the amount of transmission light at each wavelength. In this case, transmission light data at 800 nm may be used for analysis when, for example, the change in the amount of transmission light at the 800 nm wavelength is greater than the threshold value, and transmission light data at 660 nm may be used for analysis when the change in the amount of transmission light at 800 nm is less than the threshold value.

In the present embodiment, whether or not a specific wavelength can be used for analysis is determined by following order of steps: it is determined whether or not the change in the amount of transmission light at the specific wavelength exceeds a threshold; if the change in transmission light is found to be greater than the threshold value, then it is determined whether or not the transmission light during the lag phase at the particular wavelength exceeds a threshold value. However, the present invention is not limited to this configuration. For example, the order of the determination steps may be as follows: it is determined whether or not the transmission light at a specific wavelength during the lag phase exceeds a threshold value; if the amount of transmission light is found to be greater than the threshold value, then it is determined whether or not the change in the amount of transmission light at the particular wavelength exceeds a threshold value.

The present embodiment has been described in terms of the detection device and control device being provided separately. However, the present invention is not limited to this configuration inasmuch as the functions of the control device may be provided in the detection device.

The present embodiment has been described by way of example is photometric measurement (main measurement) of an analysis sample using the coagulation time method. However, the present invention is not limited to this configuration. Rather than the coagulation time method, the properties of blood coagulation of a specimen (blood sample) may be analyzed by photometric measurement of the analysis sample using a synthetic substrate method, immunoturbidity method or the like. It is also possible to analyze clinical items related to characteristics other than blood coagulation. Although plasma is used as a specimen in the present embodiment, serum may also be used according to the measurement item.

What is claimed is:

1. A blood analyzer comprising:
   a light emitter for emitting light to an analysis sample which is a mixture of a blood specimen and a reagent;
   a light receiver for receiving light of a plurality of wavelengths from the analysis sample over time, and for outputting data of an amount of the received light received at a plurality of points of time for each of the plurality of wavelengths;
   a memory encoded with the data output by the light receiver, the stored data comprising a plurality of data each corresponding to one of the plurality of wavelengths and each comprising data of the amount of the received light received by the light receiver at the plurality of points of time;
   a selector programmed to select data corresponding to one of the plurality of wavelengths from the data stored in the memory, the selecting being based on a change over time of an amount of light received, said change over time represented in the data stored in the memory; and
   an analyzer programmed to analyze a characteristic related to blood coagulation of the blood specimen using the data which are selected by the selector.

2. The blood analyzer according to claim 1, wherein the selector selects data corresponding to one wavelength among a plurality of wavelengths based on:
   an amount of received light at a point in time before the analysis sample indicates a coagulation reaction in data obtained by the light receiver; and
   the change over time in the amount of received light in data obtained by the light receiver.

3. The blood analyzer according to claim 2, wherein the selector selects data corresponding to a single wavelength among a plurality of wavelengths based on the change over time in the amount of received light when the amount of received light at a point in time before the analysis sample indicates a coagulation reaction is within the analysis range analyzable by the analysis section.

4. The blood analyzer according to claim 1, wherein the selector selects data corresponding to a first wavelength when the change over time in the amount of received light is greater than a predetermined value in data corresponding to the first wavelength obtained by the light receiver.

5. The blood analyzer according to claim 4, wherein:
   when the change over time in the amount of received light is less than a predetermined value in data corresponding to the first wavelength; and
   when the change over time in the amount of received light is greater than a predetermined value in data corresponding to a second wavelength obtained by the light receiver, then
   the selector selects data corresponding to the second wavelength obtained by the light receiver.

6. The blood analyzer according to claim 4, wherein:
   when the change over time in the amount of received light is greater than a first predetermined value in data corresponding to the first wavelength; and
   when the amount of received light at a point in time before the analysis sample indicates a coagulation reaction is, greater than a second predetermined value in data corresponding to the first wavelength, then the selector selects the data corresponding to the first wavelength.

7. The blood analyzer according to claim 6, wherein the selector determines whether or not data corresponding to the second wavelength are usable for analysis based on the amount of received light in data corresponding to the second wavelength that is shorter than the first wavelength, when the change over time in the amount of received light is less than the first value in data corresponding to the first wavelength.

8. The blood analyzer according to claim 6, wherein:
   when the change over time in the amount of received light is greater than the first predetermined value in data corresponding to the first wavelength; and
   when the amount of received light at a point in time before the analysis sample indicates a coagulation reaction is less than the second predetermined value in data corresponding to the first wavelength, then
   the selector determines whether or not data corresponding to a third wavelength are usable for analysis based on the amount of received light in data corresponding to the third wavelength that is longer than the first wavelength.

9. The blood analyzer according to claim 1, wherein the analysis section analyzes blood coagulation time as a characteristic relating to blood coagulation of the blood specimen.

10. The blood analyzer according to claim 1, wherein the blood specimen is plasma or serum.

11. A blood analyzer comprising:
    a light emitter for emitting light to an analysis sample which is a mixture of a blood specimen and a reagent;
    a light receiver for receiving light of a plurality of wavelengths from the analysis sample over time, and for outputting data of an amount of the received light received at a plurality of points of time for each of the plurality of wavelengths;
    a memory encoded with the data output by the light receiver, the stored data comprising a plurality of data each corresponding to one of the plurality of wavelengths and each comprising data of the amount of the received light received by the light receiver at the plurality of points of time;
    a selector programmed to select data corresponding to one of the plurality of wavelengths from the data stored in the memory, the selecting being based on a change over time of an amount of light received, said change over time represented in the data stored in the memory; and
    an analyzer programmed to analyze a characteristic of the blood specimen using the data which are selected by the selector.

12. A blood analyzing method comprising:
    a) emitting light to an analysis sample prepared using a blood specimen;
    b) storing data, representing an amount of light received from the blood coagulation analysis sample, at a plurality of points in time for each of a plurality of light wavelengths;
    c) selecting the stored data corresponding to one of the plurality of wavelengths, based on a change over time of the amount of light received, said change over time represented in the stored data; and
    d) analyzing a characteristic related to blood coagulation of the blood specimen using the data which are selected in step c).

13. The blood analyzing method according to claim 12, wherein the selection of data in step c) is performed based on:
    the amount of received light at a point in time before the analysis sample indicates a coagulation reaction in the data stored in step b); and the change over time in the amount of received light in data stored in step b).

14. The blood analyzing method according to claim 13, wherein the selection of data in step c) is performed based on the change over time in the amount of light received, when the amount of received light at a point in time before the analysis sample indicates a blood coagulation reaction is within the analysis range usable in step d).

15. The blood analyzing method according to claim 12, wherein the data corresponding to a first wavelength are selected in step c) when the change over time in the amount of received light is greater than a predetermined value in data corresponding to the first wavelength stored in step b).

16. The blood analyzing method according to claim 15, wherein:
when the change over time in the amount of received light is less than a predetermined value in data corresponding to the first wavelength stored in step b); and
when the change over time in the amount of received light is greater than a predetermined value in data corresponding to the second wavelength stored in step b), then
the data corresponding to a second wavelength are selected in step c).

17. The blood analyzing method according to claim 15, wherein:
when the change over time in the amount of received light is greater than a first predetermined value in data corresponding to the first wavelength acquired in step b); and
when the amount of received light at a point in time before the analysis sample indicates a coagulation reaction is greater than a second predetermined value in data corresponding to the first wavelength acquired in step b), then
the data corresponding to the first wavelength are selected in step c).

18. The blood analyzing method according to claim 17, wherein in step c), a determination is made as to whether the data corresponding to the second wavelength are usable for analysis in step d) based on the amount of received light, represented in the data corresponding to the second wavelength which is shorter than the first wavelength, when the change over time in the amount of received light is less than the first predetermined value in the data corresponding to the first wavelength.

19. The blood analyzing method according to claim 17, wherein in step c), a determination is made as to whether data corresponding to the third wavelength are usable for analysis in step d) based on the amount of received light, represented in the data corresponding to the third wavelength which is longer than the first wavelength when:
the change over time in the amount of received light is greater than the first predetermined value in data corresponding to the first wavelength; and
the amount of received light at a point in time before the analysis sample indicates a coagulation reaction is less than a second predetermined value in data corresponding to a first wavelength.

20. The blood analyzing method according to claim 12, wherein the blood coagulation time is analyzed as the characteristic related to blood coagulation of the blood specimen in step d).

21. The blood analyzing method according to claim 12, wherein the blood specimen is plasma or serum.

22. A blood analyzing method comprising:
a) emitting light to an analysis sample prepared using a blood specimen;
b) storing data, representing an amount of light received from the blood coagulation analysis sample, at a plurality of points in time for each of a plurality of light wavelengths;
c) selecting the stored data corresponding to one of the plurality of wavelengths, based on a change over time of the amount of light received light received, said change over time represented in the stored data; and
d) analyzing a characteristic of the blood specimen using the data which are selected in step c).

23. The blood analyzer of claim 1, wherein said received light of the plurality of wavelengths is received regardless of whether said wavelengths are optimal for assaying the analysis sample.

24. The blood analyzer of claim 1, wherein said selecting occurs after the analysis sample has been assayed.

* * * * *